US012508612B2

(12) United States Patent
Gomez et al.

(10) Patent No.: US 12,508,612 B2
(45) Date of Patent: Dec. 30, 2025

(54) DEVICE FOR DISPENSING A FLUID PRODUCT

(71) Applicant: APTAR FRANCE SAS, Le Neubourg (FR)

(72) Inventors: Thomas Gomez, Lyons (FR); Philippe Le Faou, Ecully (FR); Khaoula Mghimimi, Ecully (FR); Ege Tekce, Francheville (FR)

(73) Assignee: APTAR FRANCE SAS, Le Neubourg (FR)

( * ) Notice: Subject to any disclaimer, the term of this patent is extended or adjusted under 35 U.S.C. 154(b) by 244 days.

(21) Appl. No.: 18/034,744

(22) PCT Filed: Nov. 2, 2021

(86) PCT No.: PCT/FR2021/051915
§ 371 (c)(1),
(2) Date: May 1, 2023

(87) PCT Pub. No.: WO2022/090675
PCT Pub. Date: May 5, 2022

(65) Prior Publication Data

US 2023/0398561 A1 Dec. 14, 2023

(30) Foreign Application Priority Data

Nov. 2, 2020 (FR) ........................................ 2011233

(51) Int. Cl.
*B05B 11/10* (2023.01)
*A61M 11/00* (2006.01)
(Continued)

(52) U.S. Cl.
CPC ........ *B05B 11/1023* (2023.01); *A61M 5/2455* (2013.01); *A61M 5/30* (2013.01);
(Continued)

(58) Field of Classification Search
CPC ............. B05B 11/1023; B05B 11/1026; B05B 11/1053; B05B 11/0029; B05B 11/02;
(Continued)

(56) References Cited

U.S. PATENT DOCUMENTS 5,368,201 A * 11/1994 Fuchs ................. B05B 11/0027 222/320
5,893,484 A 4/1999 Fuchs et al.
(Continued)

FOREIGN PATENT DOCUMENTS

| | | | | |
|---|---|---|---|---|
| CH | 714774 B1 * | 9/2019 | ......... A61K 31/5517 |
| FR | 2858810 A1 * | 2/2005 | ....... B05C 17/00576 |
| WO | 2019/122671 A1 | 6/2019 | |

OTHER PUBLICATIONS

International Preliminary Report on Patentability (with translation of Written Opinion) dated May 2, 2023 in International Application No. PCT/FR2021/051915.
(Continued)

*Primary Examiner* — Paul R Durand
*Assistant Examiner* — Michael C Patterson
(74) *Attorney, Agent, or Firm* — Sughrue Mion, PLLC

(57) ABSTRACT

A fluid product dispensing device having a reservoir with a dose of fluid product, a piston-stopper mounted to slide in the reservoir, a dispensing head with a dispensing orifice axially movable to move the piston-stopper to dispense the fluid product. The piston-stopper has a hollow sleeve with a central receiving zone substantially at the axial and radial center of the piston plug. A shut-off element is positioned in the central receiving zone in a shutting-off position and, during actuation, expelled from the shutting-off position towards an open position. The central receiving zone is extended axially on one side by a lower receiving zone having two wall parts separated by at two axially extending radial grooves, the wall parts holding the shut-off element in
(Continued)

its open position, with the fluid product able, during actuation, to flow from the reservoir around the shut-off element in the open position towards the dispensing orifice.

20 Claims, 3 Drawing Sheets

(51) Int. Cl.

| | |
|---|---|
| ***A61M 15/00*** | (2006.01) |
| ***A61M 15/08*** | (2006.01) |
| ***B05B 11/00*** | (2023.01) |
| ***B05B 11/02*** | (2023.01) |
| *A61M 5/24* | (2006.01) |
| *A61M 5/30* | (2006.01) |
| *A61M 5/315* | (2006.01) |

(52) U.S. Cl.
CPC ........ *A61M 5/31511* (2013.01); *A61M 11/007* (2014.02); *A61M 15/0028* (2013.01); *A61M 15/0036* (2014.02); *A61M 15/0043* (2014.02); *A61M 15/08* (2013.01); *A61M 2202/0468* (2013.01); *B05B 11/0029* (2013.01); *B05B 11/02* (2013.01)

(58) Field of Classification Search
CPC .............. A61M 15/08; A61M 15/0028; A61M 15/007; A61M 11/006; A61M 5/2455; A61M 5/31511; A61M 5/30; A61M 15/0036; A61M 2202/0468; A61M 11/007; A61M 15/0043; A61C 17/02–028
USPC .............................. 222/224, 80, 81, 321.7–9
See application file for complete search history.

(56) References Cited

U.S. PATENT DOCUMENTS

| | | | | |
|---|---|---|---|---|
| 6,345,737 | B1 * | 2/2002 | Martin | B05B 11/02 222/320 |
| 6,398,074 | B1 * | 6/2002 | Bruna | B05B 11/062 222/386 |
| 6,425,499 | B1 * | 7/2002 | Guiffray | A61M 11/007 604/91 |
| 7,654,418 | B2 * | 2/2010 | Law | B05B 11/1061 222/321.9 |
| 9,010,584 | B2 * | 4/2015 | Law | B05B 11/1074 604/249 |
| 9,682,391 | B2 * | 6/2017 | Baillet | A61M 11/02 |
| 2021/0369992 | A1 * | 12/2021 | Norrant | A61M 15/08 |

OTHER PUBLICATIONS

International Search Report for PCT/FR2021/051915, dated Feb. 14, 2022.

* cited by examiner

DEVICE FOR DISPENSING A FLUID PRODUCT

CROSS REFERENCE TO RELATED APPLICATIONS

This application is a National Stage of International Application No. PCT/FR2021/051915 filed Nov. 2, 2021, claiming priority based on French Patent Application No. 2011233 filed Nov. 2, 2020.

FIELD OF INVENTION

The present invention relates to a device for dispensing a fluid product, in particular of the single-dose or two-dose type.

BACKGROUND

More particularly, the present invention relates to a device for dispensing a fluid product including a fluid product dispensing head for dispensing one or two doses of a pharmaceutical fluid product. In that type of device, generally referred to as a single-dose or two-dose device, each dose of fluid product, which is generally a liquid, is dispensed or sprayed through a dispensing orifice while the device is being actuated manually. If the device is a single-dose device, all of the fluid product is dispensed in a single actuation. If the device is a two-dose device, the fluid product is dispensed in two successive actuations of the device.

Generally, that type of single-dose or two-dose device is used for dispensing fluid product nasally, orally, or sublingually. For nasal dispensing, the dispensing head then includes an axial extension that is adapted to penetrate into a user's nostril during use.

That type of device may present certain drawbacks.

Thus, devices of the single-dose or two-dose type generally use a hollow needle, generally made of metal, to pierce the stopper during actuation. However, the use of a metal needle is expensive, and makes the recycling of the device after use more complex. Furthermore, when the stopper is pierced by the needle, particles of elastomer can become detached from the stopper and pollute the fluid that is dispensed.

Another problem arises when a piston-stopper is used, which, at rest, acts as a stopper and, during actuation, as a piston. To ensure good sealing at rest, a strong interaction between the outer radial surface of the piston-stopper and the inner cylindrical wall of the reservoir is desirable, but such a strong interaction risk impeding the displacement of the piston-stopper during actuation. Conversely, a weak interaction promotes easy actuation, but potentially generates sealing problems at rest. A good compromise is not easy to find, and because of the manufacturing tolerances of both the piston-stopper and the reservoir, the reproducibility of the properties is not ensured.

Documents U.S. Pat. No. 5,893,484 and WO2019122671 describe devices of the state of the art.

NON-LIMITING OBJECTS AND ADVANTAGES OF THE INVENTION

The object of this invention is to provide a device for dispensing a fluid product that does not have the above-mentioned disadvantages.

Another object of the present invention is thus to provide a device for dispensing a fluid product which ensures a perfect sealing at rest as well as easy actuation, independently of manufacturing tolerances.

Another object of the present invention is thus to provide a device for dispensing a fluid product that avoids any risk of generating polymer particles during actuation.

Another object of the present invention is to provide such a device for dispensing a fluid product that is simple and inexpensive to manufacture and to assemble.

The present invention thus provides a fluid product dispensing device comprising a reservoir containing at least one dose of fluid; a piston-stopper mounted with the ability to slide in said reservoir in order to dispense the fluid product; a dispensing head provided with a dispensing orifice and able to move axially with respect to said reservoir so as to move said piston-stopper in said reservoir in order thus to dispense the fluid product through said dispensing orifice; said piston-stopper comprising a hollow sleeve provided with a central receiving zone positioned substantially at the axial and radial centre of said piston-stopper, a shut-off element being positioned in said central receiving zone in a shutting-off position and during actuation being expelled from said shutting-off position towards an open position, said central receiving zone being extended axially on one side by a lower receiving zone comprising at least two wall parts separated by at least two radial grooves extending axially, said wall parts of said lower receiving zone retaining said shut-off element in its open position, with the fluid product being able, during actuation, to flow from said reservoir around said shut-off element in the open position through said radial grooves towards said dispensing orifice.

Advantageously, said piston-stopper comprises an upper receiving zone comprising at least two wall parts separated by at least two radial grooves extending axially, said upper receiving zone being symmetrical relative to said lower receiving zone, such that said piston-stopper is symmetrical and can be used equally well in one direction or the other.

Advantageously, each reception zone has a slightly conical shape flaring radially outwards from the central reception zone.

Advantageously, the maximum inside diameter of said wall parts is situated at the outer axial edge of each upper and lower receiving zone, said maximum inside diameter being substantially identical to the maximum outside diameter of said shut-off element.

Advantageously, each receiving zone comprises four wall parts and four radial grooves distributed over the periphery.

Advantageously, said piston-stopper comprises an outer sealing portion, formed on the outer periphery of said hollow sleeve, said sealing portion comprising at least one peripheral bead which provides sealing against an inner side wall of said reservoir.

Advantageously, said shut-off element, in the shutting-off position, exerts a radial force on said external sealing portion, increasing the interaction between said piston-stopper and said reservoir and therefore the sealing, and during actuation, when said shut-off element is expelled from its shutting-off position, the interaction between said piston-stopper and said reservoir decreases, thus facilitating the movement of said piston-stopper in said reservoir during actuation.

Advantageously, said shut-off element is spherical, such as a ball.

Advantageously, said central receiving zone is defined between an upper narrowing and a lower narrowing, such that in the shutting-off position, there are two peripheral sealing surfaces between said sealing element and said piston-stopper.

Advantageously, said dispensing head includes a dispensing channel that connects an opening tip to said dispensing orifice, said opening tip co-operating with said shut-off element during actuation so as to move it from its shutting-off position to its open position, said opening tip including one or more openings at its axial end, such as holes or slots, that enable fluid product to pass when said opening tip is in contact with said shut-off element.

Advantageously, said reservoir contains two doses of fluid product, dispensed during two successive actuations.

Alternatively, said reservoir contains one single dose of fluid product, dispensed during one single actuation.

BRIEF DESCRIPTION OF THE DRAWINGS

These advantages and characteristics of the present invention, and others, appear more clearly from the following detailed description, given by way of non-limiting examples, and with reference to the accompanying drawings, and in which.

DETAILED DESCRIPTION OF NON-LIMITING EMBODIMENTS

Figure 1:
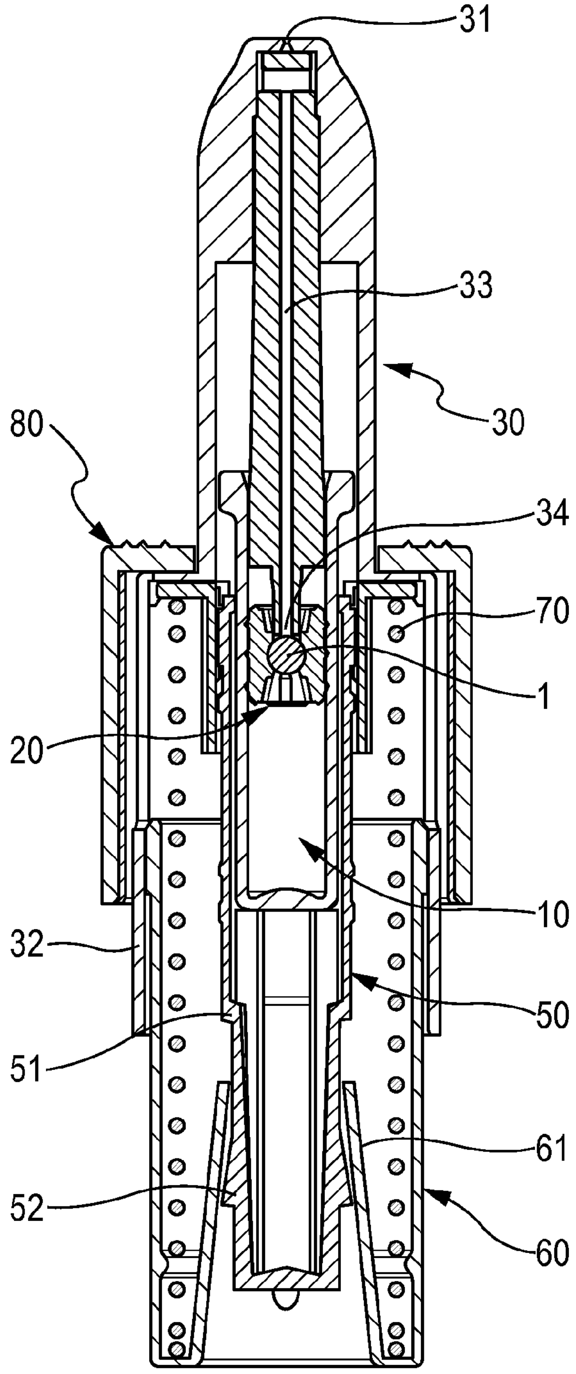
FIG. 1 is a diagrammatic section view of a fluid product dispensing device in an advantageous embodiment, shown in its rest position before dispensing the first dose.
Figure 2:
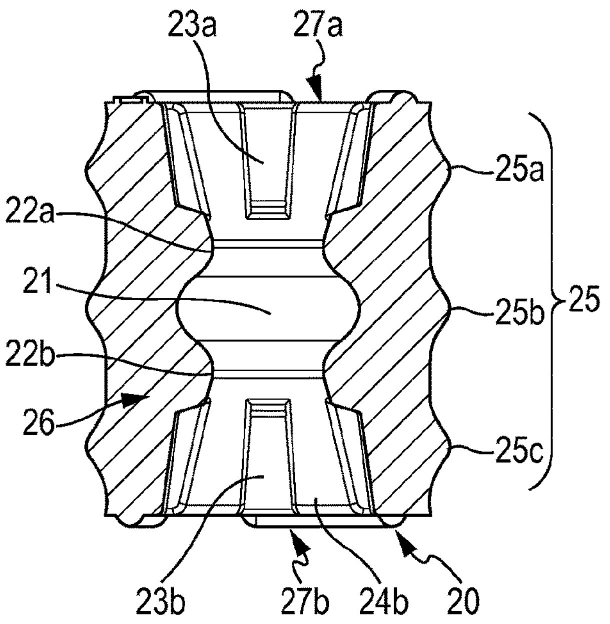
FIG. 2 is a detail of section view of the piston-stopper, the shut-off element being not assembled.

The present invention is described below with reference to a two-dose embodiment, i.e. a device containing two doses of fluid to be dispensed during two successive actuations of the device. It is however understood that the present invention could apply to single-dose devices comprising only a single dose, or to devices containing more than two doses, for example three or four doses. In addition, the two-dose type device shown in the drawings is only one possible embodiment to which the present invention applies, and naturally the present invention applies more generally to any type of device containing at least one dose.

Referring to FIG. 1, the two-dose dispensing device includes a reservoir 10 containing two doses of fluid product. A piston-stopper 20 is mounted with the ability to slide in said reservoir 10. In the pre-actuation position of the device, shown in FIG. 1, said piston-stopper 20 acts as a stopper, isolating the contents of the reservoir 10.

The piston-stopper 20 comprises a hollow sleeve 26 provided with a central receiving zone 21 disposed substantially at the axial and radial center of said piston-stopper 20, intended to receive a shut-off element 1 in the shutting-off position.

The shut-off element 1 is preferably spherical, such as a ball. This shut-off element 1 can be made of any appropriate material, such as, for example, a synthetic material, a metal, a ceramic or glass.

Figure 3:
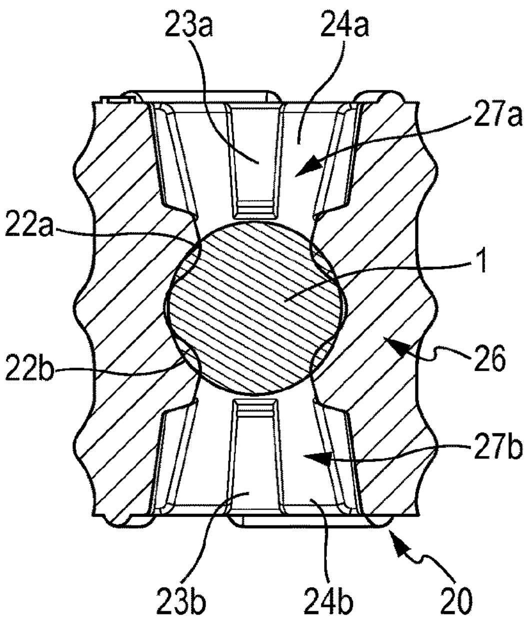
FIG. 3 is a view similar to the view in FIG. 2 with the shut-off element assembled in the shutting-off position.
Figure 4:
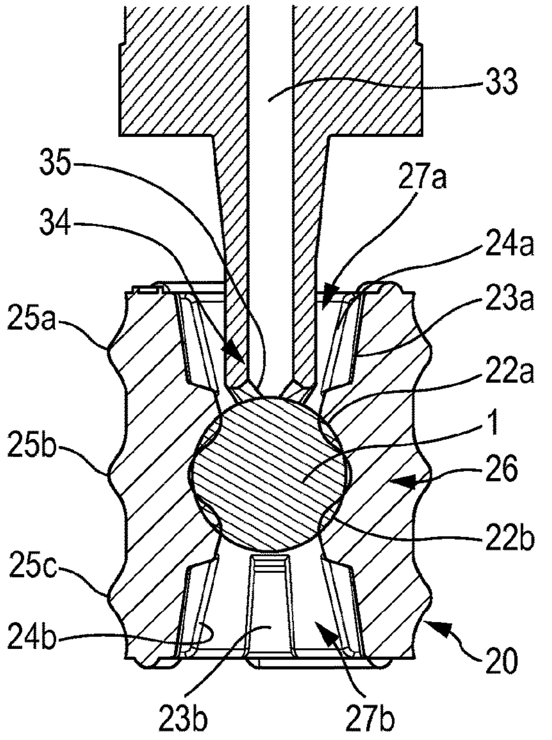
FIG. 4 is a view similar to the view in FIG. 3 with the shut-off element assembled in the shutting-off position.

The central receiving zone 21 is defined between an upper narrowing 22*a* and a lower narrowing 22*b*, so that when the shut-off element 1 is arranged in said central receiving zone 21, there are two peripheral sealing surfaces between the shut-off element 1 and the piston-stopper 20, a first sealing surface being formed by the upper narrowing 22*a* and the second sealing surface being formed by the lower narrowing 22*b*, as illustrated in FIGS. 3 and 4. The sealing in the shutting-off position of the shut-off element 1 is therefore ensured, and this shutting-off position is particularly stable.

The central receiving zone 21 is extended axially on one side by a lower receiving zone 27*b*. Advantageously, the central reception zone 21 is extended axially on the opposite side by an upper reception zone 27*a*, symmetrical to the lower reception zone 27*b*. Advantageously, each reception zone 27*a*, 27*b* has a slightly conical shape flaring radially outwards from the central reception zone 21. Each receiving zone 27*a*, 27*b* comprises wall parts 24*a*, 24*b* separated by radial grooves 23*a*, 23*b* extending axially. In the example of the figures, there are four wall parts 24*a*, 24*b* and four radial grooves 23*a*, 23*b* distributed over the periphery, but it is possible to envisage any number of wall parts and of radial grooves.

Because of the conical shape flaring radially outwards from the central receiving zone 21, the maximum inside diameter of said wall parts 24*a*, 24*b* is situated at the outer axial edge of each upper and lower receiving zone 27*a*, 27*b*. Preferably, said maximum inside diameter is substantially identical to the maximum outside diameter of the shut-off element 1.

During assembly, the shut-off element 1 is inserted by force into the central receiving zone 21, in the shutting-off position. Advantageously, in the embodiment described, the shut-off element 1 is firstly disposed in the upper receiving zone 27*a*, and then it is inserted by force into the central receiving zone 21, in the shutting-off position.

During actuation, the shut-off element 1 is mechanically expelled from the central receiving zone 21, as described in greater detail below, and it then comes to be positioned in the lower receiving zone 27*b*, so as to be held there in an open position by said wall parts 24*b*. In this open position, the fluid product can flow around said shut-off element 1 via the radial grooves 23*b*. Holding the shut-off element 1 in the piston-stopper 20 after it has been expelled from its shutting-off position is advantageous in that it makes it possible to limit the dead volume induced by the lower receiving zone 27*b*. This also makes it possible to avoid any risk of the piston-stopper 20 being plugged up again.

The piston-stopper 20 includes an outer sealing portion 25, formed on the outer periphery of the hollow sleeve 26. In the example of the figures, this sealing part 25 comprises three peripheral beads, an upper bead 25*a*, a central bead 25*b* and a lower bead 25*c*, which provide the sealing against the inner lateral wall of the reservoir 10. Of course, any number of beads could be provided, for example a single bead, two beads or more than three beads.

In the shutting-off position of the shut-off element 1, the latter exerts a radial force on the upper and lower narrowings 22*a*, 22*b*, which will at least partially be transmitted radially to said external sealing part 25, which will increase the interaction and therefore the sealing between the piston-stopper 20 and the reservoir 10. During actuation, when the shut-off element 1 is expelled from its shutting-off position, this radial force decreases or even disappears, and consequently the interaction between the piston-stopper 20 and the reservoir 10 also decreases, which facilitates the displacement of the piston-stopper 20 in the reservoir 10 during actuation. Advantageously, the displacement of the piston-stopper 20 in the reservoir 10 during actuation begins only after the shut-off element 1 has been expelled from its shutting-off position.

As can be seen in the figures, the piston-stopper 20 is advantageously perfectly symmetrical and can therefore be used equally well in one direction or the other. This reversible nature of the piston-stopper 20 is advantageous, in particular during assembly. In fact, it is not necessary to orientate the piston-stopper 20 in a particular direction, such that the assembly of the piston-stopper 20 is simplified and therefore less expensive.

A dispensing head 30 is mounted on the reservoir 10, being axially movable relative thereto. In particular, an axial movement of the dispensing head 30 relative to the reservoir 10 causes the piston-stopper 20 to move in the reservoir 10, and thus the dispensing of the fluid product contained in said reservoir. The dispensing head 30 includes a dispensing channel 33 that extends from an opening tip 34 to the dispensing orifice 31 of the dispensing head 30. During actuation, the opening tip 34 engages with the shut-off element 1 so as to move it from its shutting-off position towards its open position. A spray profile, which may be of any known type and not shown in more detail in the drawings, can be provided upstream of the dispensing orifice 31 for dispensing fluid in spray form.

At its axial end, the opening tip 34 may include one or more openings 35, such as holes or slots, that enable fluid to pass when the opening tip 34 is in contact with the shut-off element 1. Alternatively, the end of said opening tip 34 could have a shape that is suitable for allowing the fluid product to pass during actuation.

In the example shown, the reservoir 10 is fastened in a body 50 that is thus secured to said reservoir 10 and that moves together with it.

The dispensing head 30 includes a bottom side skirt 32 that is adapted to engage with an actuating member 60. A finger-rest element 80 is assembled around said dispensing head 30, or, alternatively, may be formed integrally therewith.

Said actuating member 60 is axially movable inside said side skirt 32 of the dispensing head 30 so as to perform successive actuations of the device. To this end, the actuating member 60 includes at least one sloping tab 61 that is adapted to engage with projections 51, 52 of the body 50 so as to perform successive actuations.

A return spring 70 is mounted between the actuating member 60 and the dispensing head 30 so as to return said actuating member 60 into its start position after each actuation.

Typically, the axial force needed to expel the shut-off element 1 from its shutting-off position is about from 2 N to 8 N, and advantageously from 4 N to 6 N. The axial force needed to move the piston-stopper 20 in the reservoir 10 with the shut-off element 1 in its shutting-off position is typically between about 10 N and 15 N. Thus, expelling the shut-off element 1 from its shutting-off position does not move the piston-stopper 20, with this displacement starting only when the shut-off element 1 is in its open position. After the shut-off element has been expelled from its shutting-off position, the force needed to displace the piston-stopper 20 decreases, typically to between 2 N and 10 N, thereby making it easier for the user to actuate. The present invention therefore makes it possible to reinforce the sealing at rest, while making it easier to actuate the device. Moreover, because the force necessary to expel the shut-off element 1 from its shutting-off position is less than the force necessary to move the piston-stopper 20 in the reservoir 10 with the shut-off element 1 in the shutting-off position, there is no risk of overcompression of the fluid product, and therefore the distance travelled by the piston-stopper 20 corresponds to the expelled dose volume, which, in the case of a two-dose, makes it possible to achieve good volume equilibrium between the two doses.

Figure 5:
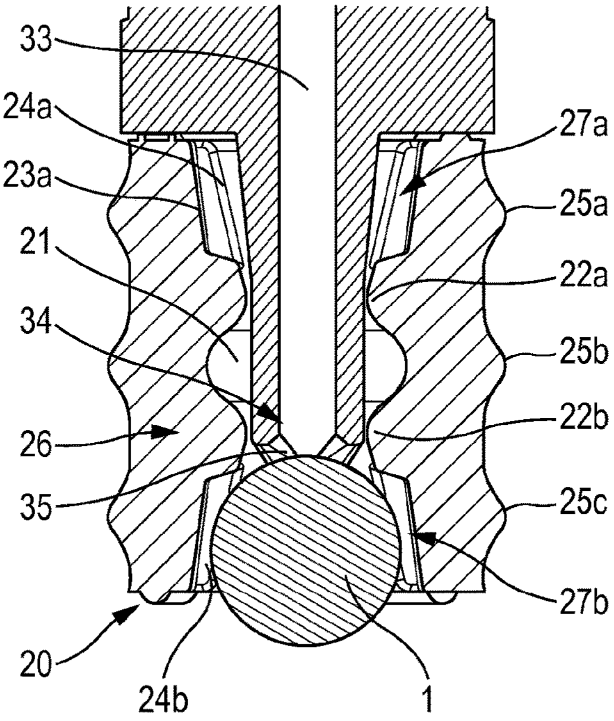
FIG. 5 is a view similar to the view in FIG. 4 with the shut-off element assembled in the open position.
Figure 6:
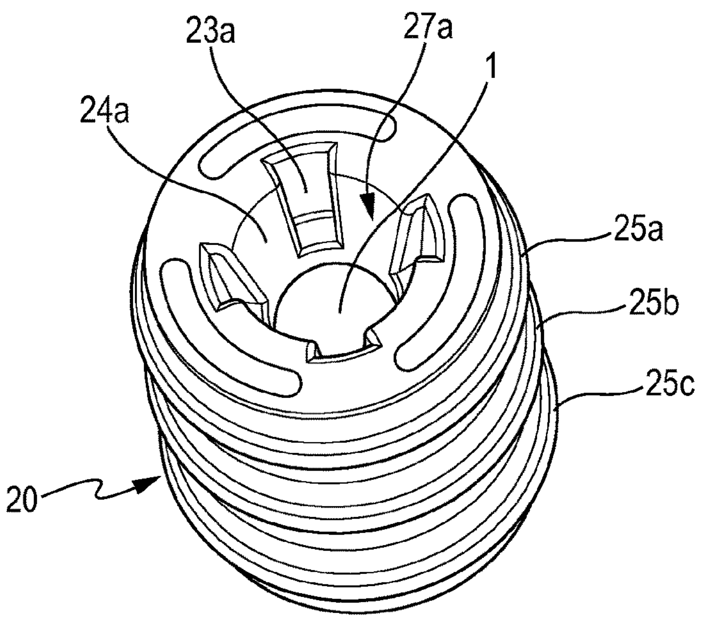
FIG. 6 is a schematic perspective view of the piston stopper, with the closure element in the closure position.
Figure 7:
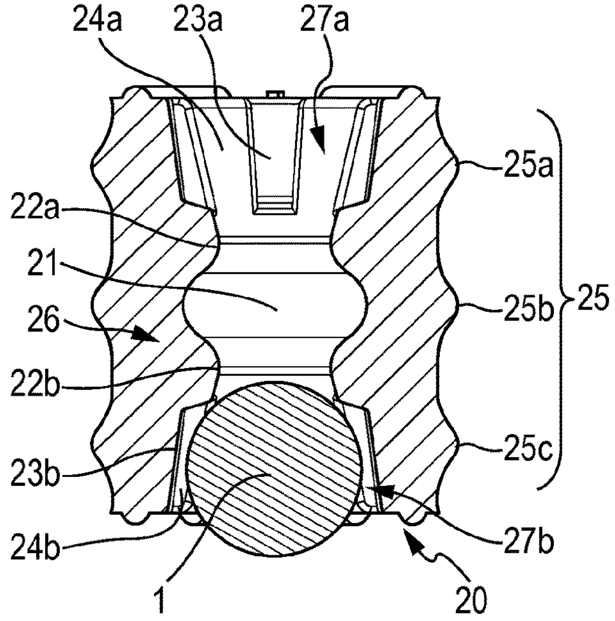
FIG. 7 is a view similar to the view in FIG. 3 with the shut-off element assembled in the open position.
Figure 8:
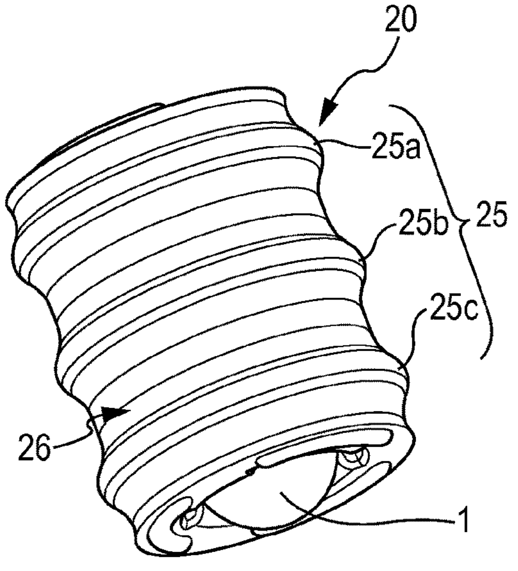
FIG. 8 is a schematic perspective view of the piston stopper, with the closure element in the open position, In the description below, the terms "axial" and "radial" are relative to the longitudinal central axis of the device. The terms "upper" and "lower" refer to the upright position of the piston-stopper represented in Figures.

Operation of the device shown in FIG. 1 is as follows. In the rest position in FIG. 1, the piston-stopper 20 isolates the contents of the reservoir 10 from the atmosphere. When the user presses simultaneously on the finger rest 80 and on the actuating member 60, said actuating member 60 moves inside the side skirt 32 of the dispensing head 30. This pushes the body 50 axially upwards from the position shown in FIG. 1, by means of the tabs 61 that push on the shoulder 51 of said body. This compresses the spring 70 and moves the reservoir 10 relative to the dispenser head 30. When the reservoir 10 starts to move relative to the dispensing head 30, the opening tip 34 of the dispensing channel 33 comes to expel the shut-off element 1 from its closure position, visible in FIGS. 1, 3, 4 and 6, to its opening position, visible in FIGS. 5, 7 and 8, so as to put the inside of the reservoir 10 into communication with said dispensing channel 33. Further actuation will cause the piston-stopper 20 to move within the container 10 and thus a dispensing of a first dose. The fluid is thus pushed by said piston-stopper 20 around the shut-off element 1 through the opening tip 34 and into the dispensing channel 33, then via the spray profile and out of the device through the dispensing orifice 31.

After the first dose has been dispensed, when the user releases the actuating member 60, the spring 70 returns it towards its start position. While the actuating member 60 is returning, the reservoir and the body 50 do not move back, since the two components remain held in said dispensing head 30. Optionally, the dispensing head 30 may include non-return means, so as to prevent said body 50 and/or said reservoir 10 from moving back. When the actuating member 60 returns towards its rest position, the tabs 61 come to be positioned below the second projection 52 of the body 50, which enables the user to actuate the device a second time, so as to dispense the second dose of fluid.

The present invention is described above with reference to an embodiment that is not limiting, and any useful modification can be applied to the present invention without going beyond its ambit, as defined by the accompanying claims.

The invention claimed is:

1. A fluid product dispensing device comprising a reservoir containing a fluid product in an amount of at least one dose, a piston-stopper mounted with the ability to slide in said reservoir in order to dispense the fluid product, a dispensing head, provided with a dispensing orifice, and able to move axially with respect to said reservoir so as to move said piston-stopper in said reservoir in order thus to dispense the fluid product through said dispensing orifice, said piston-stopper comprising a hollow sleeve provided with a central receiving zone arranged in said piston-stopper, a shut-off element being positioned in said central receiving zone in a shutting-off position and being, during actuation, expelled from said shutting-off position towards an open position, wherein said central receiving zone is extended axially on one side by a lower receiving zone comprising at least two wall parts separated by at least two grooves extending axially and radially relative to an axis of the central receiving zone, said wall parts of said lower receiving zone holding said shut-off element in the open position, with the fluid product being able, during actuation, to flow from said reservoir around said shut-off element in the open position via said grooves towards said dispensing orifice; and wherein said piston-stopper comprises an upper receiving zone comprising at least two wall parts separated by at least two grooves extending axially and radially relative to an axis of the central receiving zone, said upper receiving zone being symmetrical relative to said lower receiving zone, such that said piston-stopper is symmetrical.

2. The device according to claim 1, wherein each of the lower receiving zone and the upper receiving zone flares radially outwards from the central receiving zone.

3. The device according to claim 2, wherein, for the upper receiving zone, a maximum inside diameter of said wall parts of said upper receiving zone is situated at an outer axial edge of the upper receiving zone; and wherein, for the lower receiving zone, a maximum inside diameter of said wall parts of said lower receiving zone is situated at an outer axial edge of the lower receiving zone.

4. The device according to claim 3, wherein each maximum inside diameter is the same as a maximum outside diameter of said shut-off element.

5. The device according to claim 1, wherein each of the lower receiving zone and the upper receiving zone comprises four wall parts and four grooves distributed over a respective periphery of the lower receiving zone and the upper receiving zone.

6. The device according to claim 1, wherein said piston-stopper comprises an outer sealing part, formed on an outer periphery of said hollow sleeve, said outer sealing part comprising at least one peripheral bead which provides sealing against an inner side wall of said reservoir.

7. The device according to claim 6, wherein said shut-off element, in the shutting-off position, exerts a radial force on said outer sealing part, increasing the interaction between said piston-stopper and said reservoir and therefore the sealing, and during actuation, when said shut-off element is expelled from the shutting-off position, the interaction between said piston-stopper and said reservoir decreases, thus facilitating the movement of said piston-stopper in said reservoir during actuation.

8. The device according to claim 1, wherein said shut-off element is spherical.

9. The device according to claim 1, wherein said shut-off element is a ball.

10. The device according to claim 1, wherein said central receiving zone is defined between an upper narrowing and a lower narrowing, such that in the shutting-off position, there are two peripheral sealing surfaces between said shut-off element and said piston-stopper.

11. The device according to claim 1, wherein said dispensing head includes a dispensing channel that connects an opening tip to said dispensing orifice, said opening tip co-operating with said shut-off element during actuation so as to move said shut-off element from the shutting-off position to the open position, said opening tip including one or more openings at an axial end of said opening tip that enable the fluid product to pass when said opening tip is in contact with said shut-off element when in the open position.

12. The device according to claim 11, wherein said one or more openings at the axial end of said opening tip are holes or slots.

13. The device according to claim 1, wherein said reservoir contains two doses of the fluid product, dispensed in two successive actuations.

14. The device according to claim 1, wherein said reservoir contains one single dose of the fluid product, dispensed in one single actuation.

15. The device according to claim 1, wherein said hollow sleeve provided with the central receiving zone is arranged at an axial and radial centre of said piston-stopper.

16. A fluid product dispensing device comprising a reservoir containing a fluid product in an amount of at least one dose, a piston-stopper mounted with the ability to slide in said reservoir in order to dispense the fluid product, a dispensing head, provided with a dispensing orifice, and able to move axially with respect to said reservoir so as to move said piston-stopper in said reservoir in order thus to dispense the fluid product through said dispensing orifice, said piston-stopper comprising a hollow sleeve provided with a central receiving zone arranged in said piston-stopper, a shut-off element being positioned in said central receiving zone in a shutting-off position and being, during actuation, expelled from said shutting-off position towards an open position, wherein said central receiving zone is extended axially on one side by a lower receiving zone comprising at least two wall parts separated by at least two grooves extending axially and radially relative to an axis of the central receiving zone, said wall parts of said lower receiving zone holding said shut-off element in the open position, with the fluid product being able, during actuation, to flow from said reservoir around said shut-off element in the open position via said grooves towards said dispensing orifice;

wherein said piston-stopper comprises an outer sealing part, formed on the outer periphery of said hollow sleeve, said outer sealing part comprising at least one peripheral bead which provides sealing against an inner side wall of said reservoir; and wherein said shut-off element, in the shutting-off position, exerts a radial force on said outer sealing part, increasing the interaction between said piston-stopper and said reservoir and therefore the sealing, and during actuation, when said shut-off element is expelled from the shutting-off position, the interaction between said piston-stopper and said reservoir decreases, thus facilitating the movement of said piston-stopper in said reservoir during actuation.

17. The device according to claim 16, wherein the lower receiving zone flares radially outwards from the central receiving zone.

18. A fluid product dispensing device comprising a reservoir containing a fluid product in an amount of at least one dose, a piston-stopper mounted with the ability to slide in said reservoir in order to dispense the fluid product, a dispensing head, provided with a dispensing orifice, and able to move axially with respect to said reservoir so as to move said piston-stopper in said reservoir in order thus to dispense the fluid product through said dispensing orifice, said piston-stopper comprising a hollow sleeve provided with a central receiving zone arranged in said piston-stopper, a shut-off element being positioned in said central receiving zone in a shutting-off position and being, during actuation, expelled from said shutting-off position towards an open position, wherein said central receiving zone is extended axially on one side by a lower receiving zone comprising at least two wall parts separated by at least two grooves extending axially and radially relative to an axis of the central receiving zone, said wall parts of said lower receiving zone holding said shut-off element in the open position, with the fluid product being able, during actuation, to flow from said reservoir around said shut-off element in the open position via said grooves towards said dispensing orifice; and wherein said dispensing head includes a dispensing channel that connects an opening tip to said dispensing orifice, said opening tip co-operating with said shut-off element during actuation so as to move said shut-off element from the shutting-off position to the open position, said opening tip including one or more openings at an axial end of said opening tip that enable the fluid product to pass when said opening tip is in contact with said shut-off element when in the open position.

19. The device according to claim 18, wherein the lower receiving zone flares radially outwards from the central receiving zone.

20. The device according to claim 18, wherein the lower receiving zone comprises four wall parts and four grooves distributed over a periphery of the lower receiving zone.

* * * * *